(12) United States Patent
Levy et al.

(10) Patent No.: US 9,744,254 B2
(45) Date of Patent: Aug. 29, 2017

(54) CASE FOR SANITIZING AND TRANSPORTING TATTOO MACHINES

(71) Applicants: Darren Levy, North Fort Myers, FL (US); Frank Levy, Fort Myers, FL (US)

(72) Inventors: Darren Levy, North Fort Myers, FL (US); Frank Levy, Fort Myers, FL (US)

( * ) Notice: Subject to any disclaimer, the term of this patent is extended or adjusted under 35 U.S.C. 154(b) by 0 days.

(21) Appl. No.: 15/148,727

(22) Filed: May 6, 2016

(65) Prior Publication Data
US 2016/0250364 A1 Sep. 1, 2016

Related U.S. Application Data

(63) Continuation-in-part of application No. 14/278,329, filed on May 15, 2014, now Pat. No. 9,339,105, (Continued)

(51) Int. Cl.
| | |
|---|---|
| *G01N 21/00* | (2006.01) |
| *G01N 23/00* | (2006.01) |
| *A61N 5/00* | (2006.01) |
| *A61L 2/10* | (2006.01) |
| *B65D 43/16* | (2006.01) |
| *B65D 43/22* | (2006.01) |
| *B65D 25/28* | (2006.01) |

(Continued)

(52) U.S. Cl.
CPC *A61L 2/10* (2013.01); *A45C 5/03* (2013.01); *A45C 11/00* (2013.01); *A45C 11/008* (2013.01); *A45C 15/00* (2013.01); *A45C 15/06* (2013.01); *A61L 2/24* (2013.01); *A61M 37/0076* (2013.01); *B65D 25/28* (2013.01); *B65D 43/16* (2013.01); *B65D 43/22* (2013.01); *H05B 37/0281* (2013.01); *A45C 2005/037* (2013.01); *A45D 2200/205* (2013.01); *A45D 2200/25* (2013.01); *A61M 2209/10* (2013.01)

(58) Field of Classification Search
CPC ....... B01J 19/00; A61L 2/0035; A61L 2/0047; A61L 2/10
USPC ................ 422/24; 250/492.1, 494.1, 455.11, 250/453.11
See application file for complete search history.

(56) References Cited

U.S. PATENT DOCUMENTS

| | | | |
|---|---|---|---|
| 4,135,269 | A | 1/1979 | Marston |
| 5,160,699 | A | 11/1992 | Siegal |

(Continued)

FOREIGN PATENT DOCUMENTS

| | | |
|---|---|---|
| CN | 2879757 Y | 3/2007 |
| CN | 102759810 B | 12/2013 |
| WO | WO2008/155793 A2 | 12/2008 |

OTHER PUBLICATIONS

U.S. Appl. No. 15/091,010, Multi-Head Artist and Make-Up Brush.

*Primary Examiner* — Monzer R Chorbaji
(74) *Attorney, Agent, or Firm* — Welsh Flaxman & Gitler LLC

(57) ABSTRACT

A storage and sterilizing case shaped and dimensioned for storing a tattoo machine therein. The case has a cover and a base. The cover is connected to the base via a hinge securing the cover to the base along adjacent edges thereof. The base includes a tray for supporting the tattoo machine within the case. The interior of the case is provided with an electronic circuit board and at least one ultraviolet light.

12 Claims, 3 Drawing Sheets

Related U.S. Application Data which is a continuation-in-part of application No. 12/608,709, filed on Oct. 29, 2009, now abandoned, which is a continuation-in-part of application No. 11/432,443, filed on May 11, 2006, now abandoned.

(60) Provisional application No. 62/157,747, filed on May 6, 2015.

(51) Int. Cl.
| | | |
|---|---|---|
| *A61M 37/00* | (2006.01) | |
| *A61L 2/24* | (2006.01) | |
| *H05B 37/02* | (2006.01) | |
| *A45C 11/00* | (2006.01) | |
| *A45C 15/00* | (2006.01) | |
| *A45C 5/03* | (2006.01) | |
| *A45C 15/06* | (2006.01) | |

(56) References Cited

U.S. PATENT DOCUMENTS

| | | | |
|---|---|---|---|
| 6,039,928 A * | 3/2000 | Roberts | A61L 2/10 422/186.3 |
| 6,461,568 B1 | 10/2002 | Eckhardt | |
| 6,821,355 B1 | 11/2004 | Taylor et al. | |
| 7,207,242 B1 * | 4/2007 | Daigle | A61M 37/0076 30/362 |
| 8,158,961 B2 | 4/2012 | Merkle | |
| 8,481,970 B2 | 7/2013 | Cooper et al. | |
| 8,964,405 B2 | 2/2015 | LaPorte et al. | |
| 9,339,576 B2 | 5/2016 | LaPorte et al. | |
| 2003/0034459 A1 | 2/2003 | Bonin | |
| 2006/0175554 A1 | 8/2006 | Riddell | |

\* cited by examiner

CASE FOR SANITIZING AND TRANSPORTING TATTOO MACHINES

CROSS REFERENCE TO RELATED APPLICATION

This application claims the benefit of U.S. Provisional Patent Application Ser. No. 62/157,747, entitled "CASE FOR SANITIZING AND TRANSPORTING TATTOO MACHINES," filed May 6, 2015, and this application is a continuation-in-part of U.S. patent application Ser. No. 14/278,329, entitled "MULTI-HEAD ARTIST AND MAKE-UP BRUSH," filed May 15, 2014, which is currently pending, which is a continuation-in-part of U.S. patent application Ser. No. 12/608,709, entitled "MULTI-HEAD ARTIST AND MAKE-UP BRUSH," filed Oct. 29, 2009, which is currently pending, which is a continuation-in-part of U.S. patent application Ser. No. 11/432,443, entitled "MULTI-HEAD ARTIST AND MAKE-UP BRUSH," filed May 11, 2006, which is abandoned, the disclosures of which are incorporated herein by reference in their entirety.

BACKGROUND OF THE INVENTION

1. Field of the Invention

The present invention relates generally to a case for a tattoo artist, and more specifically to a tattoo artist case including a plurality of tattoo machines allowing for transport and sanitizing thereof in a convenient and reliable manner.

2. Description of the Related Art

While it is required to replace needles used with tattoo liners and tattoo shaders for each person getting a tattoo, the actual machines themselves are not replaced for each person getting a tattoo. However, these machines are brought into close proximity with many individuals and it is, therefore, possible for diseases to be transmitted from one person to another by using a tattooing machine that has not been properly cleaned between uses.

The present invention attempts to remedy this by providing a case in which tattooing machines may be stored, carried and sanitized.

SUMMARY OF THE INVENTION

It is, therefore, an object of the present invention to provide a storage and sterilizing case shaped and dimensioned for storing a tattoo machine. The case has a cover and a base. Each of the cover and the base include a concave construction such that when the case is closed the cover and base define an enclosed space, the cover being connected to the base via a hinge securing the cover to the base along adjacent edges thereof such that the cover may be selectively moved between an open configuration where contents of the case are exposed and a closed configuration where contents of the case are fully enclosed within the case. The base includes a tray for supporting the tattoo machine within the case. The case further includes an electronic circuit board and at least one ultraviolet light.

It is also an object of the present invention to provide storage and sterilizing case including a tattoo machine.

It is another object of the present invention to provide storage and sterilizing case wherein the at least one ultraviolet light includes four 5 inch ultraviolet bulbs within poly(methyl methacrylate) casings.

It is a further object of the present invention to provide storage and sterilizing case wherein the cover is substantially rectangular in shape and includes first and second short side walls and first and second long side walls depending from the cover wall, as well as an external surface and an interior surface on opposite sides of the cover; and the base is rectangular in shape and includes first and second short side walls and first and second long side walls depending from the base wall, as well as an external surface and an interior surface on opposite sides of the base; wherein when in the closed configuration the short side walls and long side walls of the cover align with the short side walls and long side walls of the base with the respective external surfaces of the cover and the base facing away from each other, and wherein two of the ultraviolet lights are secured along the interior surface of the base along long side walls of the base, and the other two ultraviolet lights are secured along the interior surface of the cover along cover wall in alignment with the short side walls of the cover.

It is also an object of the present invention to provide storage and sterilizing case wherein an actuator transmits a signal to the electronic circuit board when the cover is closed upon the base causing power to be applied to the at least one ultraviolet light, and opening of the case interrupts the signal causing power to the at least one ultraviolet light to cease.

It is another object of the present invention to provide storage and sterilizing case wherein the electronic circuit board includes a timer which controls the timing for providing power to the at least one ultraviolet light.

It is also an object of the present invention to provide storage and sterilizing case wherein the at least one ultraviolet light functions with the following characteristics: Wattage: 0.3 W±15%; Voltage: 160V±8; Power: 1.7 mA; 254 nm output: 260 uW/cm$^2$ (at surface); Stability: 5 min; Life: 10000 hrs.

It is another object of the present invention to provide storage and sterilizing case wherein the tattoo machine includes a frame to which a tube having a grip is coupled. The tattoo machine also includes a needle positioned to extend through the inside of the tube, wherein the needle is secured to a needle drive mechanism coupled to the frame such that the needle may be moved relative to the tube in a desired manner for the application of ink to the skin of an individual.

It is a further object of the present invention to provide storage and sterilizing case wherein the case is further provided with a clasp in the form of a locking mechanism allowing for selective fastening of the case in the closed configuration and opening thereof when desired.

It is also an object of the present invention to provide storage and sterilizing case wherein the base is provided with a handle.

It is another object of the present invention to provide storage and sterilizing case wherein two of the ultraviolet lights are secured along an interior surface of the base, and the other two ultraviolet lights are secured along an interior surface of the cover.

Other objects and advantages of the present invention will become apparent from the following detailed description when viewed in conjunction with the accompanying drawings, which set forth certain embodiments of the invention.

DESCRIPTION OF THE PREFERRED EMBODIMENT

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as a basis for teaching one skilled in the art how to make and/or use the invention.

As is well appreciated by those skilled in the art, needles of tattoo machines are required to be replaced for each person getting a tattoo, however, the other components are not replaced. With reference to FIGS. 1 to 4, the present invention provides and includes a storage and sterilizing case 100 for these components. The case 100 provides convenient and reliable mechanism for storing, transporting and sanitizing the tattoo machine(s) 10 and associated accessories. As such, it is appreciated the case 100 may be configured for storing the tattoo machine 10 and/or associated accessories in either its assembled or unassembled configuration. In addition to tattoo machines, the present case is well suited for storing and sterilizing electric razors used in salons and barbershops, as well as electric razors used by pet groomers at various locations.

Figure 2:
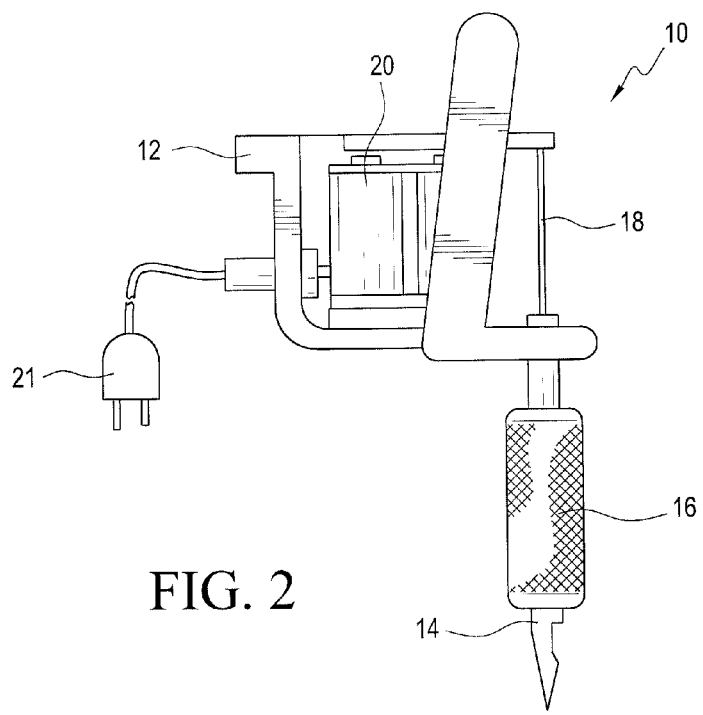
FIG. 2 is a side view of the tattoo machine contained in the storage and sterilizing case.

With reference to FIG. 2, and as those skilled in the art will appreciate, a tattoo machine 10 generally includes a frame 12 to which a tube 14 is coupled. The tube 14 includes a grip 16. A variety of tube and grip configurations are known in the art and may be employed in accordance with the present invention.

The tattoo machine 10 also includes a needle 18 positioned to extend through the inside of the tube 14. The needle 18 is secured to a needle drive mechanism 20 coupled to the frame 12 such that the needle 18 may be moved relative to the tube 14 in a desired manner for the application of ink to the skin of an individual in a manner well known to those skilled in the art. A power cable 21 extends from the frame 12 and is electronically coupled to the needle drive mechanism 20 to provide power for the operation thereof.

The needle drive mechanism 20 is adapted to drive the needle 18 upon actuation of the motor (not shown) associated with the needle drive mechanism 20. It is appreciated a variety of needle drive mechanisms are known in the art, and any of these drive mechanisms may be used in accordance with the present invention.

Figure 1:
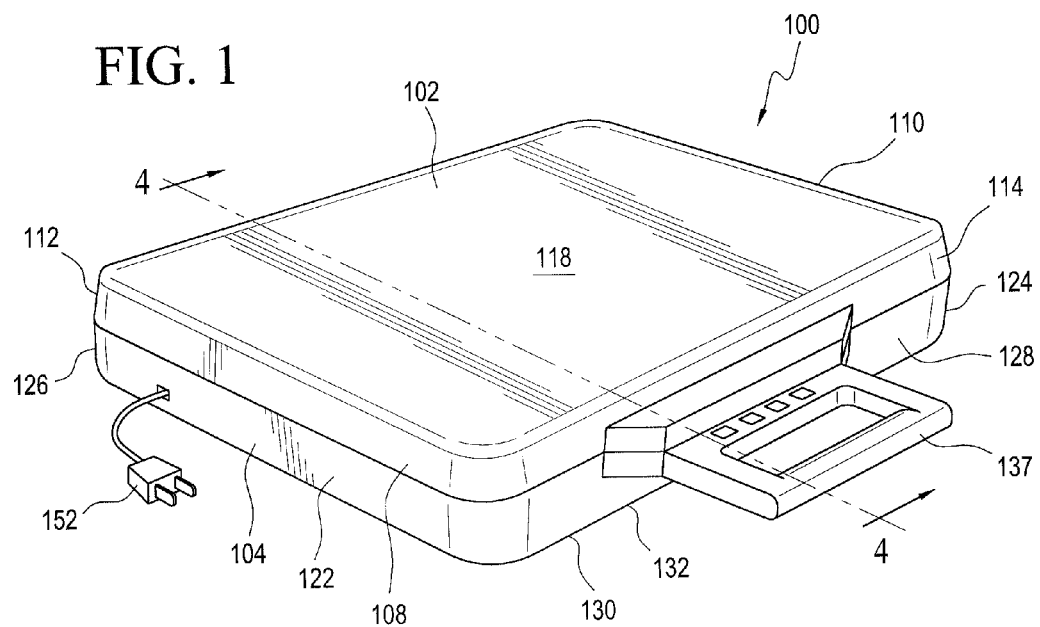
FIG. 1 is perspective view of the present storage and sterilizing case in its closed configuration with a tattoo machine contained therein.
Figure 3:
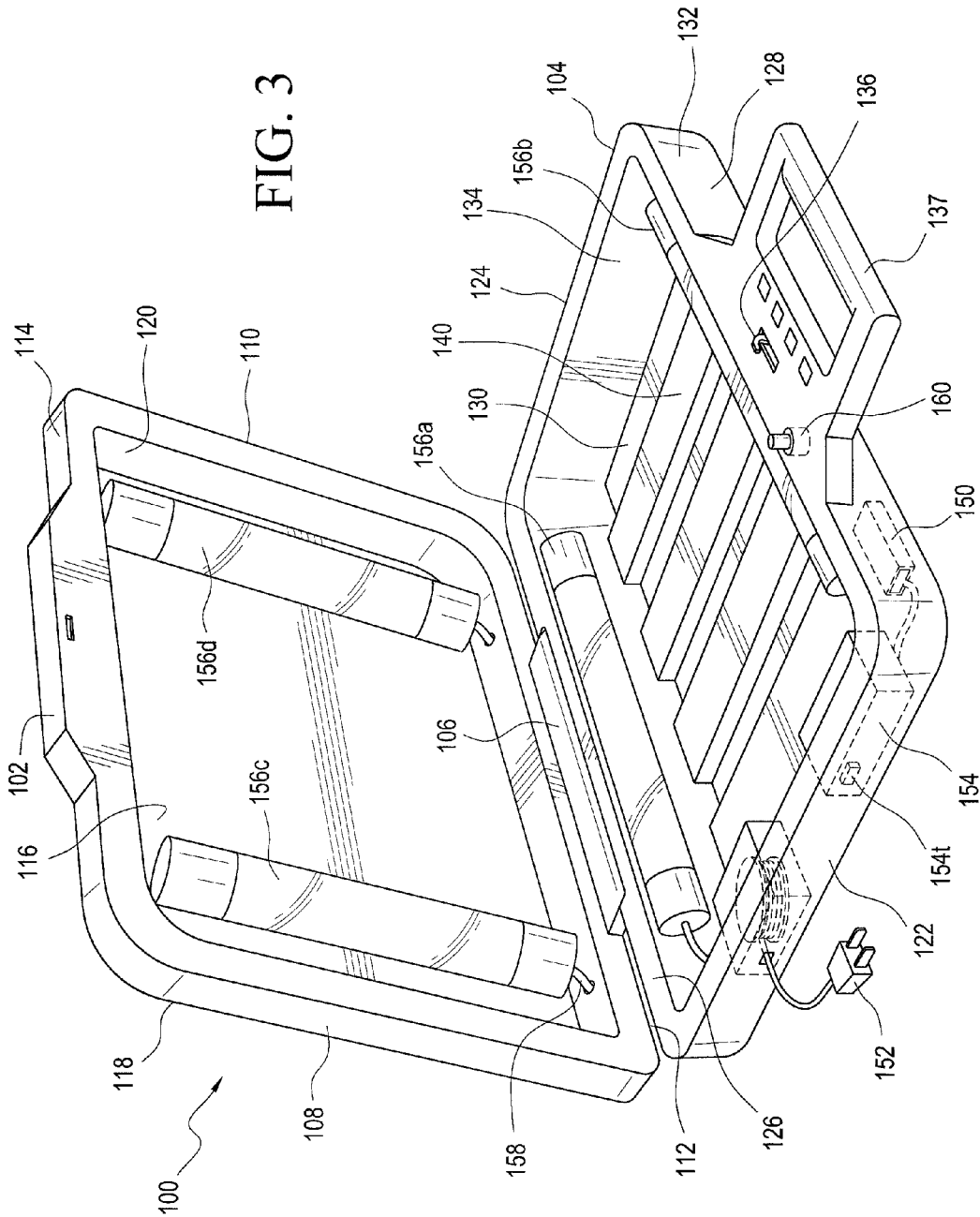
FIG. 3 is a perspective view of the storage and sterilizing case in its open configuration with the tattoo machine removed.
Figure 4:
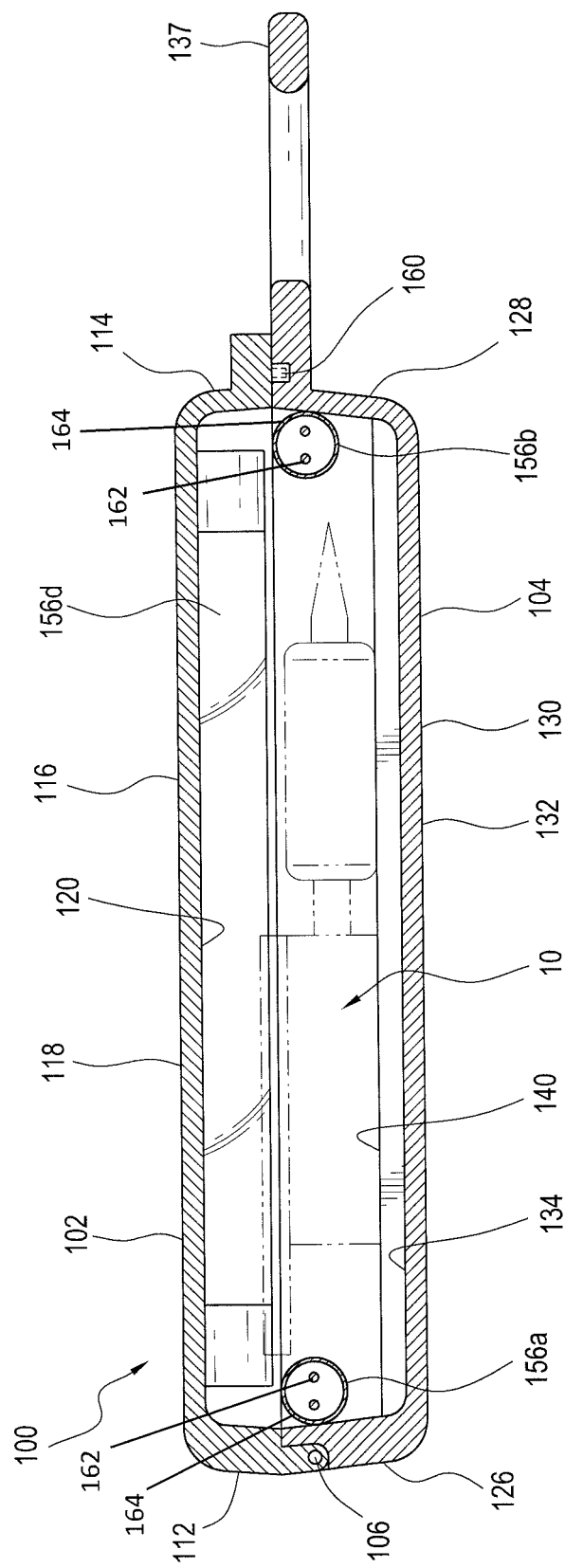
FIG. 4 is a cross sectional view along the line 4-4 in FIG. 1.

As seen in FIGS. 1, 3 and 4, the case 100 has a cover 102 and a base 104. The cover 102 is connected to the base 104 via a hinge 106 securing the cover 102 to the base 104 along adjacent edges thereof. In accordance with a preferred embodiment, both the cover 102 and the base 104 include a concave construction such that when the case 100 is closed the cover 102 and base 104 define an enclosed space.

More particularly, the base 104 and cover 102 are connected by a hinge 106 allowing for the cover 102 to move between an open configuration where the contents of the case 100 are exposed and a closed configuration where the contents of the case 100 are fully enclosed within the case 100. As will be explained below in greater detail, it is when the case 100 is in its closed configuration that that sanitizing mechanisms may be activated to sanitize the tattoo machines 10 stored therein.

The cover 102 is substantially rectangular in shape and includes first and second short side walls 108, 110 and first and second long side walls 112, 114 depending from the cover wall 116, as well as an external surface 118 and an interior surface 120 on opposite sides of the cover 102. Similarly, the base 104 is substantially the same shape as the cover 102 and is therefore rectangular in shape and includes first and second short side walls 122, 124 and first and second long side walls 126, 128 depending from the base wall 130, as well as an external surface 132 and an interior surface 134 on opposite sides of the base 104. When in the closed configuration the short side walls 108, 110 and long side walls 112, 114 of the cover 102 align with the short side walls 122, 124 and long side walls 126, 128 of the base 104 with the respective external surfaces 118, 132 of the cover 102 and the base 104 facing away from each other.

As briefly discussed above, a hinge 106 connects the base 104 to cover 102. In accordance with a preferred embodiment, the hinge 106 is formed between the first long side wall 112 of the cover 102 and the first long side wall 126 of the base 104. In this way, the first long side wall 112 of the cover 102 and the first long side wall 126 of the base 104 are held adjacent to each other as the case 100 is moved between its open configuration and its closed configuration. The second long side wall 114 of the cover 102 and the second long side wall 128 of the base 104 are, in contrast, permitted to move toward and away from each other as the case 100 moves between its closed configuration where the second long side wall 114 of the cover 102 and the second long side wall 128 of the base 104 are in contact such that the interior contents of the case 100 are hidden therein and the open configuration where the second long side wall 114 of the cover 102 and the second long side wall 128 of the base 104 are spaced from each other allowing the tattoo artist access to the contents of the case 100. The case 100 is further provided with a clasp 136 in the form of a locking mechanism allowing for selective fastening of the case 100 in a closed configuration and opening thereof when desired. The second long side wall 128 of the base 104 is also provided with a handle 137.

Access to the tattoo machines 10 held within the case 100 is achieved by providing a tray 140 within the base 104 for supporting the tattoo machine 10 and/or its parts within the case 100. It is appreciated the tray 140 may take a variety of forms. In general, it will be constructed to support the tattoo machine 10 and its associated accessories in such a manner that the tattoo machine 10 and associated accessories are fully exposed to the sterilizing ultraviolet light.

The interior of the case 100 is provided with batteries 150, retractable power cord 152, an electronic circuit board 154 and ultraviolet lights 156a-d incorporated thereon and secured into position. In accordance with a preferred embodiment, the ultraviolet lights 156a-d include four 5 inch ultraviolet bulbs 162 within PLEXIGLAS® (that is, Poly(methyl methacrylate) (PMMA), also known as acrylic or acrylic glass) casings 164 (as shown with reference to ultraviolet lights 156a-b in FIG. 4, although it is appreciated the other ultraviolet lights 156c-d are of the same construction). Two of the ultraviolet lights 156a, 156b are secured along the interior surface 134 of the base 104 in alignment with (that is, substantially parallel to) the long side walls 126, 128 of the base 104, while the other two ultraviolet lights 156c, 156d are secured along the interior surface 120 of the cover 102 along cover wall 116 in alignment with (that is, substantially parallel to) the short side walls 108, 110 of the cover 102. The electronic circuit board 154 is connected to the ultraviolet lights 156*a-d* as well as the batteries 150 or the power cord 152 via power wire 158. An actuator 160 transmits a signal to the circuit board 154 when the cover 102 is closed upon the base 104 causing power to be applied to the ultraviolet lights 156*a-d*. The signal is only transmitted when the case 100 is closed and opening of the case 100 interrupts the signal causing power to the ultraviolet lights 156*a-d* to cease. The signal initiates power from the electronic circuit board 154 to the ultraviolet lights 156*a-d* for a preset period. The electronic circuit board includes a timer 154*t* which controls the timing for the application of power to the ultraviolet lights 156*a-d*. In a preferred embodiment, ultraviolet light is illuminated for 2-5 minutes.

In accordance with a preferred embodiment, the ultraviolet lights function with the following characteristics:

Wattage: 0.3 W±15%
Voltage: 160V±8
Power: 1.7 mA
254 nm output*: 260 uW/cm$^2$ (at surface)
Stability: 5 min
Life: 10000 hrs.

* The radiant efficiency of the ultraviolet light measured at a wavelength of 254 nm based upon the fact 254 nm wavelength ultraviolet light is effective in killing bacterial agents An ultraviolet light with these characteristics produces highly desirable results as shown in Table A.

TABLE A

| Kill rate (uW · sec/cm$^2$) | | Time to kill at 1 cm target distance (seconds) |
| --- | --- | --- |
| Escherichlia coli | 6600 | 1.6 |
| Staphylococcus aureus | 6600 | 1.6 |
| Streptococcus lactis | 8800 | 2.2 |
| Infectious hepatitis | 8000 | 2.0 |
| Influenza | 6600 | 1.6 |

While the invention has been described in its preferred form or embodiment with some degree of particularity, it is understood that this description has been given only by way of example and that numerous changes in the details of construction, fabrication, and use, including the combination and arrangement of parts, may be made without departing from the spirit and scope of the invention.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A storage and sterilizing case, comprising:
a tattoo machine;
a storage and sterilizing case shaped and dimensioned for storing the tattoo machine;
the case has a cover and a base, each of the cover and the base includes a concave construction such that when the case is closed the cover and base define an enclosed space, the cover being connected to the base via a hinge securing the cover to the base along adjacent edges thereof such that the covet may be selectively moved between an open configuration where contents of the case are exposed and a closed configuration where contents of the case are fully enclosed within the case, wherein the base includes a tray for supporting the tattoo machine within the case; and the case further includes an electronic circuit board and four ultraviolet lights;
wherein the cover is substantially rectangular in shape and includes first and second short side walls and first and second long side walls depending from a cover wall, as well as an external surface and an interior surface on opposite sides of the cover; and the base is rectangular in shape and includes first and second short side walls and first and second long side walls depending from a base wall, as well as an external surface and an interior surface on opposite sides of the base; wherein when in the closed configuration the first and second short side walls and the first and second long side walls of the cover align with the first and second short side walls and the first and second long side walls of the base with the respective external surfaces of the cover and the base facing away from each other, and wherein two of the ultraviolet lights are secured along the interior surface of the base substantially parallel to the first and second long side walls of the base, and the other two ultraviolet lights are secured along the interior surface of the cover along the cover wall substantially parallel to the first and second short side walls of the cover.

2. The storage and sterilizing case according to claim 1, wherein an actuator transmits a signal to the electronic circuit board when the cover is closed upon the base causing power to be applied to the at least one ultraviolet light, and opening of the case interrupts the signal causing power to the at least one ultraviolet light to cease.

3. The storage and sterilizing case according to claim 1, wherein an actuator transmits a signal to the electronic circuit board when the cover is closed upon the base causing power to be applied to the at least one ultraviolet light, and opening of the case interrupts the signal causing power to the at least one ultraviolet light to cease.

4. The storage and sterilizing case according to claim 1, wherein the electronic circuit board includes a timer which controls the timing for providing power to the at least one ultraviolet.

5. The storage and sterilizing case according to claim 1, wherein the at least one ultraviolet light functions with the following characteristics: Wattage: 0.3 W±15%; Voltage: 160V±8; Power: 1.7 mA; 254 nm output: 260 uW/cm2 (at surface); Stability: 5 min; Life: 10000 hrs.

6. The storage and sterilizing case according to claim 1, wherein the tattoo machine includes a frame to which a tube having a grip is coupled, the tattoo machine also includes a needle positioned to extend through the inside of the tube, wherein the needle is secured to a needle drive mechanism coupled to the frame such that the needle may be moved relative to the tube in a desired manner for the application of ink to the skin of an individual.

7. The storage and sterilizing case according to claim 1, wherein the case is further provided with a clasp in the form of a locking mechanism allowing for selective fastening of the case in the closed configuration and opening thereof when desired.

8. The storage and sterilizing case according to claim 1, wherein the base is provided with a handle.

9. The storage and sterilizing case according to claim 1, wherein the at least one ultraviolet light includes four 5 inch ultraviolet bulbs within poly(methyl methacrylate) casings.

10. The storage and sterilizing case according to claim 1, wherein an actuator transmits a signal to the electronic circuit hoard when the covet is closed upon the base causing power to be applied to the at least one ultraviolet light, and opening of the case interrupts the signal causing power to the at least one ultraviolet light to cease.

11. The storage and sterilizing case according claim 1, wherein the electronic circuit board includes a timer which controls the timing for providing power to the at least one ultraviolet light.

12. The storage and sterilizing case according claim 1, wherein the at least one ultraviolet light functions with the following characteristics: Wattage: 0.3 W±15%; Voltage: 160V±8; Power: 1.7 mA; 254 nm output: 260 uW/cm2 (at surface); Stability: 5 min; Life: 10000 hrs.

* * * * *